United States Patent [19]

Mandecki et al.

[11] Patent Number: 4,936,963

[45] Date of Patent: Jun. 26, 1990

[54] POLYCATIONIC BUFFERS AND METHOD FOR GEL ELECTROPHORESIS OF NUCLEIC ACIDS

[75] Inventors: Wlodek Mandecki; Mark A. Hayden, both of Vernon Hills, Ill.

[73] Assignee: Abbott Laboratories, North Chicago, Ill.

[21] Appl. No.: 356,590

[22] Filed: May 23, 1989

Related U.S. Application Data

[63] Continuation of Ser. No. 54,645, May 27, 1987, abandoned.

[51] Int. Cl.$^5$ ............................................. G01N 27/26
[52] U.S. Cl. ............................... 204/182.8; 204/299 R
[58] Field of Search ............. 204/182.8, 299 R, 180.1

[56] References Cited

U.S. PATENT DOCUMENTS

| 4,139,440 | 2/1979 | Chrambach et al. | 204/299 R |
| 4,279,724 | 7/1981 | Hearn et al. | |
| 4,319,975 | 3/1982 | Cook | 204/182.8 |
| 4,452,901 | 6/1984 | Gordon et al. | 204/182.8 |
| 4,639,373 | 1/1987 | Babior | 424/101 |

FOREIGN PATENT DOCUMENTS

0162693A2 11/1985 European Pat. Off. .

OTHER PUBLICATIONS

Hutchens, T. William, et al., "Development of focusing Buffer Systems for Generation of Wide-Range pH Gradients During High-Performance Chromatofocusing." Journal of Chromatography, 359:157–168 (1986).

Jeffreys, Alec J., "DNA 'Fingerprint' and Segregation Analysis of Multiple Markers in Human Pedigrees." Am. J. Hum. Genet. 39:11–24, 1986.

Mandecki, Wlodek, et al., "High-Resolution Polyacrylamide Gel Electrophoresis of Oligonucleotides Using L-Histidine Buffer." DNA 7:1, 57–62, 1988.

Parkinson, Anna M., et al., "Improved Polyacrylamide Gel Electrophoresis with Different Amino Acids as the Trailing Constituent," Analytical Biochemistry, 117:6–11 (1981).

Fullarton, J. R., et al., "A Rapid System for Preparative Electrophoresis Depending on Isoelectric Buffers of Low conductivity." Biochem. J. 116:147–149 (1970).

National Technical Information Service, "New Buffers for Isoelectric focusing in electrophorasis." U.S. Department of Commerce, NTN/SP-77/1089.

Osterman, *Methods of Protein and Nucleic Acid Research,* Chapter 1, pp. 7–14 (1984).

Parkinson et al., *Analytical Biochemistry.* 117:6–11 (1981).

El-Hamalawi et al. "Effect of Polycations on the Electrophoretic Mobility of Bacterial DNA" J. Drug. Res. Egypt. vol. 16, No. 1–2 (1985) pp. 111–116.

*Primary Examiner*—John F. Niebling
*Assistant Examiner*—John S. Starsiak, Jr.
*Attorney, Agent, or Firm*—Roberta L. Hastreiter

[57] ABSTRACT

The present invention provides for polycationic buffers for the gel electrophoresis of and methods for obtaining improved separation and resolution of nucleic acids. In particular, the invention provides for a buffer consisting essentially of histidine for the gel electrophoresis of oligonucleotides ranging from a few to about 70 nucleotides in length. Polycationic buffers may be used for both analytical and preparative purposes and result in a nearly two-fold improvement in both separation and resolution of the nucleic acid bands. Furthermore, the use of polycationic buffers reduces the electrophoresis time by a factor of about three due to the low conductivity of the buffers.

4 Claims, 5 Drawing Sheets

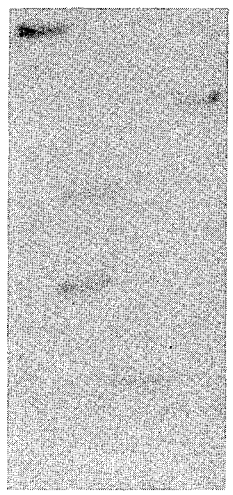

POLYCATIONIC BUFFERS AND METHOD FOR GEL ELECTROPHORESIS OF NUCLEIC ACIDS

This application is a continuation of application Ser. No. 054,645, filed May 27, 1987, now abandoned.

BACKGROUND

The present invention relates generally to polycationic buffers for high resolution gel electrophoresis of nucleic acids. More particularly, the present invention relates to the high resolution polyacrylamide gel electrophoresis of nucleic acids comprising oligonucleotides of about 2–70 nucleotides in length using L-histidine buffer.

Polyacrylamide gel electrophoresis, under denaturing conditions, is one of the most widely used methods for separating nucleic acids. The method is used to analyze mixtures of nucleic acids, as well as to purify them on a preparative scale. The term nucleic acids or oligonucleotides, as used herein, includes both single and double-stranded DNA and RNA.

A prevalently used electrophoresis buffer for nucleic acids has been described by Peacock and Dingman. Peacock, A. and Dingman, C. W., Molecular Weight Estimation and Separation of Ribonucleic Acid by Electrophoresis in Agarose-Acrylamide Composite Gels, *Biochemistry*, 7:668–674 (1968). This buffer, 89 mM Tris-borate, 2 mM EDTA, at pH 8.3, provides adequate separation of DNA or RNA but has disadvantages associated with its use. For example, the buffer's relatively high conductivity makes the entire separation process a lengthy procedure and, in addition, the separation between bands obtained using this Tris-borate buffer is less than the maximal separation theoretically possible. Accordingly, there is a need for a buffer which would give improved separation and resolution of nucleic acids on gel electrophoresis.

Although electrophoretic separation of nucleic acids is not disclosed, the separation of hemoglobins by substituting one of several amino acids, including isoleucine, alanine, valine, histidine, threonine and serine, in the place of glycine, in a discontinuous buffer system utilizing two buffers, the buffer in the upper tank having a higher pH than the buffer in the lower tank, is disclosed in Parkinson, et al., *Anal. Biochem.*, 117:6–11 (1981). The amino acid substitution, at a concentration of 192 mM is stated 1) to alter the running pH of the gel and 2) to change the propagation rate of the moving front, the former modifying the absolute mobility of the proteins and the latter modifying their relative mobilities. The migration distances and the degree of separation is reported to vary from greatest to least as follows: L-isoleucine > DL-alanine > L-alanine > DL-valine > glycine > L-histidine > DL-threonine > L-serine.

SUMMARY OF THE INVENTION

The present invention provides for polycationic buffers for obtaining improved separation and resolution of nucleic acids. In particular, the invention provides for a buffer consisting essentially of histidine for the gel electrophoresis of nucleic acids ranging in length from a few to about 70 nucleotides long. Preferably, the buffer is histidine. Other polycationic buffers contemplated by the invention include spermidine and ethylenediamine. These polycationic buffers of the invention may be used for both analytical and preparative purposes and result in a nearly two-fold improvement in both the separation and the resolution of nucleic acids. Furthermore, the use of these polycationic buffers reduces the gel electrophoresis time by a factor of about three due to the low conductivity of the buffers.

Other aspects and advantages of the present invention will be apparent upon consideration of the following detailed description thereof which includes numerous illustrative examples of practice of the invention.

BRIEF DESCRIPTION OF DRAWINGS

FIG. 1c is a densitometer scan of the gel of FIG. 1a;

FIG. 5 is a photographic illustration of fragments of autoradiograms of gels run with (a) Tris-borate buffer at 8% polyacrylamide gel cross-linking, and (b) 50 mM histidine buffer at 12% polyacrylamide gel cross-linking.

DETAILED DESCRIPTION

Figures 1A, 1B:
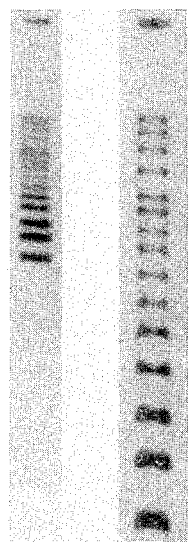
FIG. 1a is a photographic illustration of a gel prepared and run according to the prior art.
FIG. 1b is a photographic depiction of a gel prepared and run according to the present invention.

The motion of DNA molecules through the three-dimensional network of an electrophoresis gel has been suggested to involve a reptation mechanism (a reptile-like movement). deGennes, P. G., Scaling Concepts of Polymer Physics, (New York: *Cornell University Press*), pp. 223–231 (1979). The quantitative relationship between the electrophoretic mobility of DNA in gels and the length of the DNA is given by the following formula:

$$\mu = \frac{c}{\lambda^\alpha}$$

where $\mu$ is the electrophoretic mobility; $\Xi$ is the length of DNA; $\alpha$ is a constant which depends primarily upon the buffer used and its concentration; and c is a multiplicative constant which varies according to the degree of cross-linking in the gel and other experimental factors. Lerman, L. S. and Frish, H. L., Why does the electrophoretic mobility of DNA in gels vary with the length of the molecule?, *Biopolymers*, 21:995–997 (1982).

For an ideal Gaussian chain, theoretically the exponent $\alpha$ is unity. However, for typical buffers the value obtained experimentally for $\alpha$ is less than one. Plotting the logarithm of the distance migrated against the logarithm of the DNA length, a straight line is obtained with the slope equal to $\alpha$. The slope, $\alpha$, is a measure of the degree of separation obtained. When comparing two gels with different $\alpha$, and on which DNA has migrated approximately the same distance from the top of the gel, the spacing between the proximal bands is proportional to $\alpha$. Accordingly, to obtain maximum resolution it is desirable to use gels characterized by a high numerical value for α, provided that the half-width of the band does not increase, thereby reducing sharpness.

The dependence of the slope, α, upon buffer concentration and gel composition is complex and varies depending upon the gel, the buffer and the range of DNA lengths under consideration. In general, the effects of changing the gel and the buffer compositions may not be reliably predicted but must be experimentally determined.

It has been discovered that L-histidine may be used as the single solute in a buffer for the electrophoresis of oligonucleotides shorter than 70 nucleotides long for both analytical and preparative purposes. The improvement in resolution of DNA, as defined by the ratio of the spacing between bands to the band half-width, is about two-fold. In addition to improved resolution, histidine gels allow for the reduction of the electrophoresis time by a factor of about three which may be due to the low conductivity of 50 mM L-histidine.

The following examples are for illustrative purposes and are not intended in any way to limit the scope of the invention.

EXAMPLE 1

A. Oligonucleotide Markers

Synthetic oligonucleotides ranging in length from 12 to 48 nucleotides long were obtained from American Bionetics, Emeryville, Calif., and were radiolabeled according to the supplier's protocol. Another set of oligonucleotides was generated in four DNA sequencing reactions [Smith, A. J. H., In: Methods in Enzymology, 65, part I; L. Grossman and K. Moldave, eds. (New York: *Academic Press*) pp. 560–580 (1980)] using the C5a gene cloned in M13 phage [Mandecki, W., Mollison, K. W., Bolling, T. J., Powell, B. S., Carter, G. W. and Fox, J. L., Chemical Synthesis of a Gene Encoding the Human Complement Fragment C5a and its expression in *Escherichia coli., Proc. Nat'l. Acad. Sci. U.S.A.*, 82:3543–3547 (1985)] as a template.

B. Histidine Gel Preparation

To prepare a 12% acrylamide, 50 mM L-histidine denaturing gel (100 ml final volume), 0.77 g L-histidine (Sigma, St. Louis, Mo.), 30 ml of deionized solution containing 40% acrylamide and 2% N,N'-methylene-bis-acrylamide (BIS), 42 g of urea, 0.6 ml of 10% ammonium persulfate and 36 ml of water are mixed together, dissolved, and de-gassed. After 30 μl of N,N,N',N'-tetramethylenediamine (TEMED) is added, the gel is poured and allowed to polymerize for about 1 hour. Typically, a vertical 200 mm×200 mm×1.5 mm slab gel is poured; however, the dimensions may easily be changed depending on the particular application. The tank buffer is 50 mM L-histidine 7.7 g per liter) at its isoelectric point (pH 7.6). No adjustment of pH is required. To remove ammonium persulfate ions from the gel, the gel is pre-electrophoresed for about 1 hour. Completion of pre-electrophoresis is indicated by the stabilization of the current.

EXAMPLE 2

Sample Preparation and Gel Running

DNA in 50% formamide, plus appropriate dyes if desired, is heated at 100° C. for 3 minutes and then cooled on ice. The sample is then loaded onto a preelectrophoresed gel of Example 1. Because of the low conductivity of the histidine buffer, up to 3 times higher voltages than those required using standard gel buffer, are acceptable during electrophoresis. However, the temperature of the gel is maintained so as not to exceed approximately 40° C. If the temperature does exceed 40° C., a significant browning reaction will be observed which will obscure visualization of the DNA bands by UV shadowing. This browning reaction does not obscure visualization via autoradiography, however. On a 12% acrylamide gel with 50 mM L-histidine, an oligonucleotide 10 residues long (10-mer) runs with bromophenol blue, and a 30-mer runs with xylene cyanol.

EXAMPLE 3

Comparison of Resolution Obtained

Figure 1D:
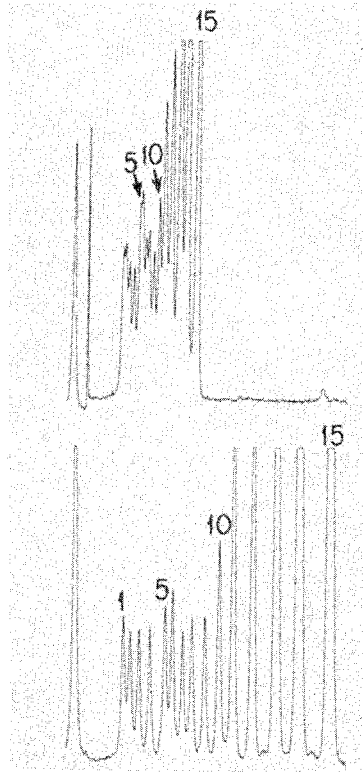
FIG. 1d is a densitometer scan of the gel of FIG. 1b.

This example demonstrates the greatly improved resolution of oligonucleotides obtained using 50 mM histidine buffer, as described in Example 1, except that a 20% polyacrylamide gel was used, as compared to the resolution obtained using the standard Tris-borate buffer. These results are depicted in FIG. 1. The lengths of the 15 oligonucleotides used as markers are: 48, 44, 40, 36, 32, 30, 28, 26, 24, 22, 20, 18, 16, 14 and 12. FIG. 1a is a 20% acrylamide gel, 89 mM Tris-borate pH 8.3 gel, (the abbreviation ORI indicates the top of the gel); FIG. 1b is 20% acrylamide, 50 mM histidine gel; and FIGS. 1c and 1d are optical densitometer scans of lanes a and b, respectively.

Figure 2:
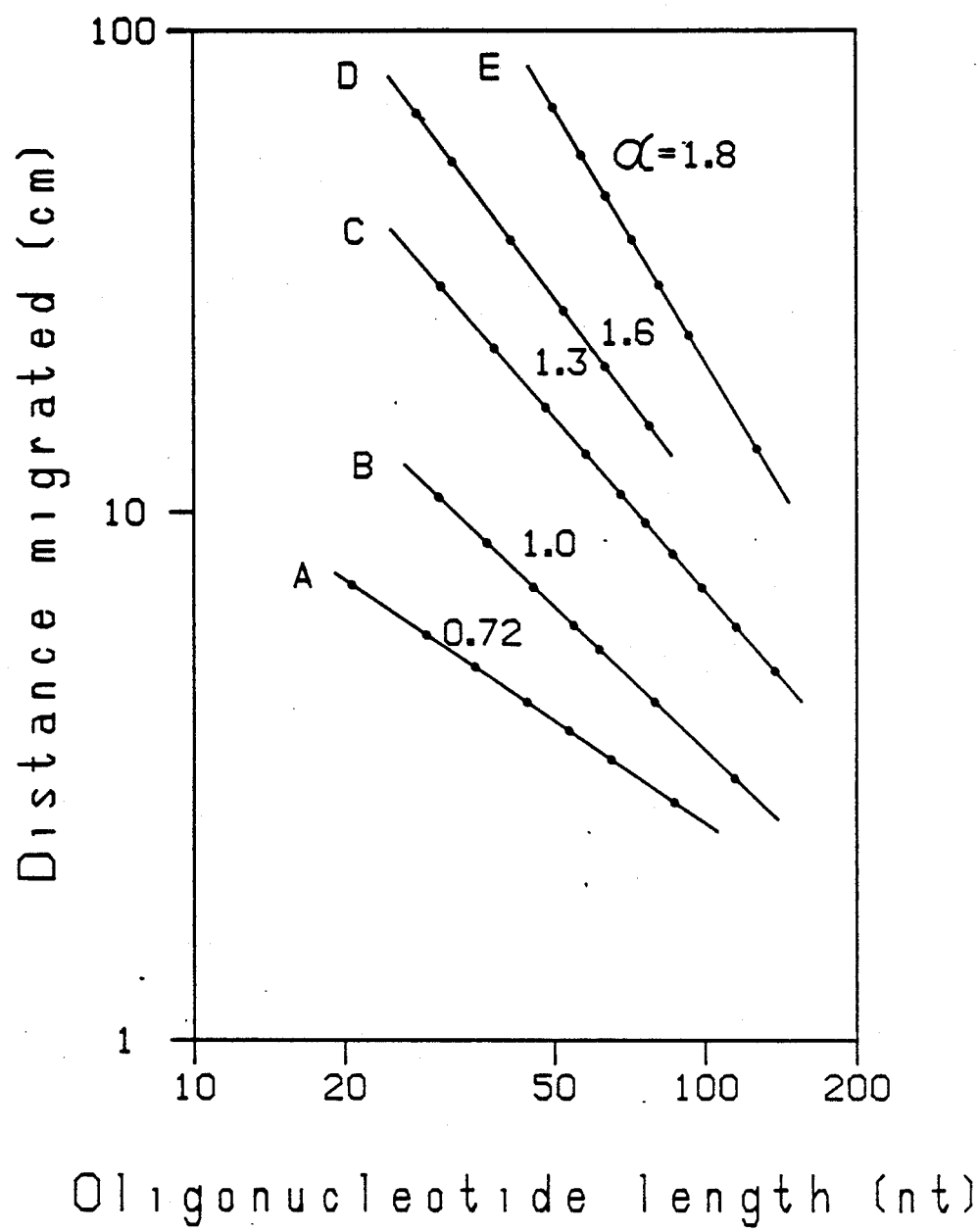
FIG. 2 is a plot of the logarithm of the distance migrated versus the logarithm of the oligonucleotide length obtained for gel electrophoresis runs using various types of buffer and of polyacrylamide concentrations.

The spacing between the bands that migrated comparable distances on both gels, i.e., bands 1 and 2, was approximately two times greater on the histidine gel than on the standard Tris-borate gel. A plot of the logarithm of distance migrated versus the logarithm of oligonucleotide length is given in FIG. 2. Numerical values of the slope, α, are indicated for each line in FIG. 2. The types of buffer and acrylamide concentrations were, respectively; A - 89 mM Tris-borate, 2 mM EDTA 20% acrylamide; B - 100 mM histidine, 15% acrylamide; C - 50 mM histidine, 12% acrylamide; D - 20 mM histidine, 12% acrylamide; and E - 10 mM histidine, 12% acrylamide. The slope, α, was calculated and for the Tris-borate gel, α was 0.72 and for histidine gel C, α was 1.3 over the range of from 20 to 150 nucleotides.

EXAMPLE 4

Optimization of Histidine Buffer Concentration and Gel Concentration

Figure 3:
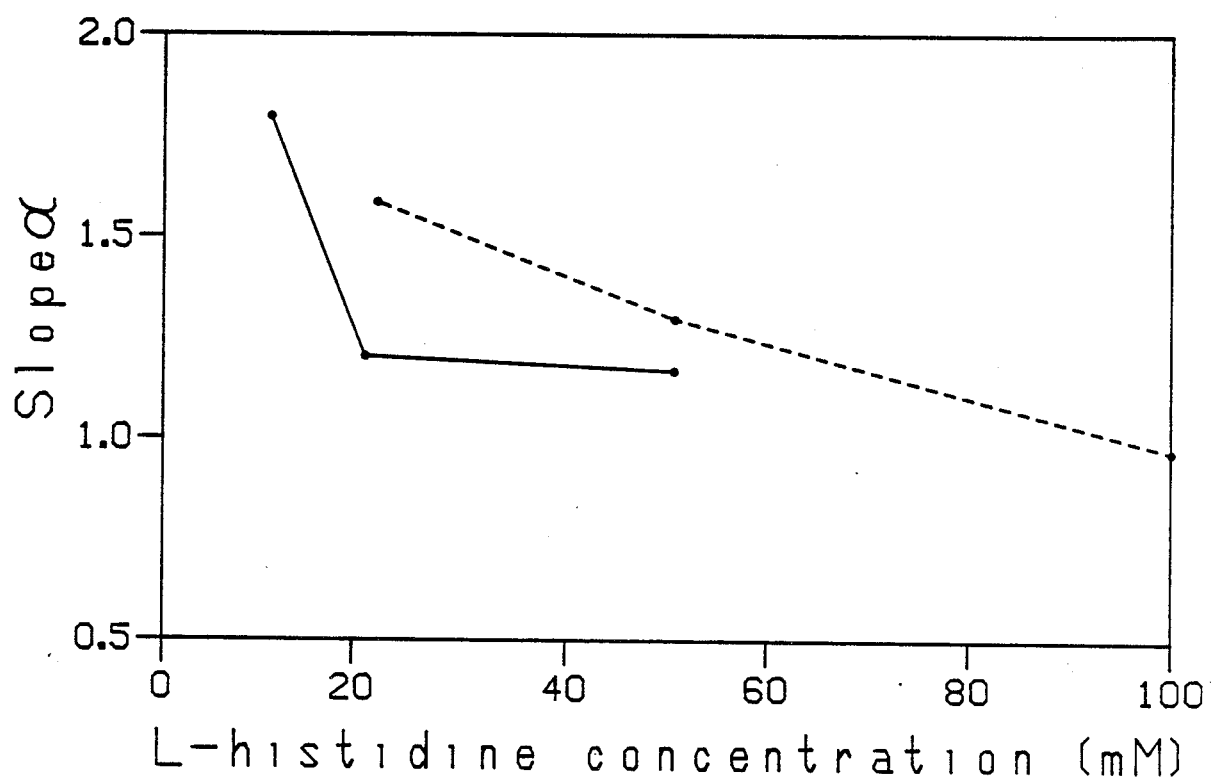
FIG. 3 is a plot of the slope, α, versus the L-histidine buffer concentration obtained using two different polyacrylamide concentrations.

This example relates to the optimization of both the histidine buffer and gel concentration in obtaining maximum separation and resolution of the bands. Multiple gels were run using various concentrations of histidine buffer (10 mM to 100 mM), and the slope, α, was calculated and plotted as shown in FIG. 3. The polyacrylamide gel percent cross-linking was 12% (solid line) and 15% (dashed line). A slope, α, greater than 1 was obtained at all concentrations of histidine buffer and at both percentages of cross-linked acrylamide gel.

Figure 4:
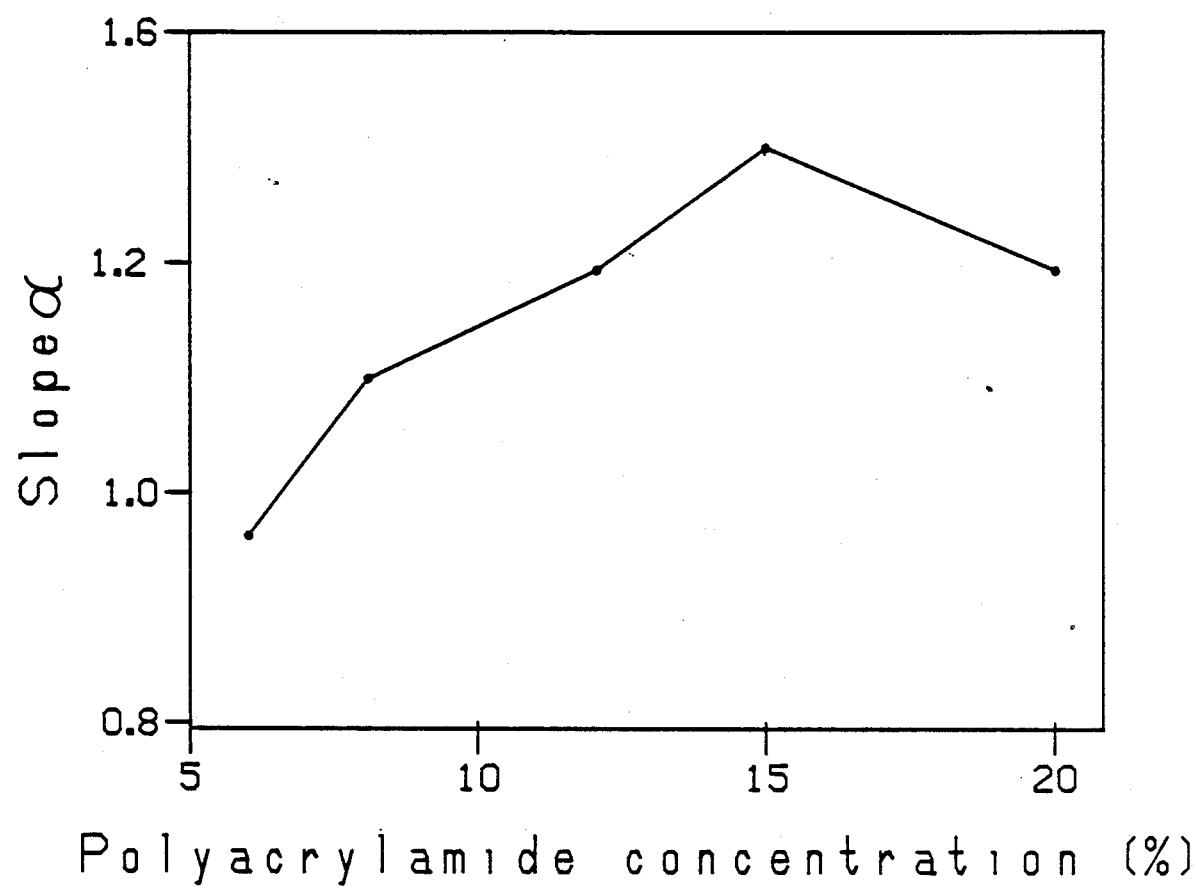
FIG. 4 is a plot of the α values obtained for varying concentrations of polyacrylamide with L-histidine buffer concentration constant at 50 mM.

FIG. 4 depicts the α values obtained when the polyacrylamide percent cross-link concentration is varied while the L-histidine concentration is kept constant at 50 mM. At all polyacrylamide concentrations studied, the slope, α, exceeded that typically obtainable for the standard Tris-borate gel.

When the polyacrylamide concentration of the gel is varied and the L-histidine concentration is kept constant, the slope, α, assumes its maximum at 15% polyacrylamide. However, lower polyacrylamide concentrations, such as 8% or 12%, are preferably used to reduce the electrophoresis time. When the histidine concentration is varied and the percent polyacrylamide is kept constant at 12%, α assumes its maximum at 20 mM histidine or less (FIG. 3). Nevertheless, 50 mM histidine is a preferred buffer concentration because of occasional gel artifacts obtained using histidine concentrations lower than 50 mM.

EXAMPLE 5

Band half-width

This example demonstrates that an improved separation of the bands is obtained using histidine gels, while the DNA bands are as sharp as on the Tris-borate gel. The sharpness of a band is judged by its half-width and the resolving power of a gel may be quantitatively described as a ratio between the slope, α, and the bandwidth. A meaningful comparison of relative band sharpness can be made by comparing those bands which have migrated the same distance and which also contain the identical oligonucleotide length.

Fragments of autoradiograms of sequencing gels with (a) 89 mM Tris-borate, 2 mM EDTA buffer, or (b) 50 mM L-histidine buffer are shown in FIG. 5. The acrylamide concentration was 8% (a) and 12% (b). The lengths of the oligonucleotides are as indicated. On both gels, the 31 nucleotide length oligonucleotide migrated the same absolute distance, i.e., 360 mm.

From FIGS. 1c, 1d, and FIG. 5, it is estimated, by direct measurements from scans, that the half-width of a DNA band, corresponding to an oligonucleotide length of between 10 and 50 nucleotides, is approximately the same for both Tris-borate and histidine gels. Given that the spacing between the DNA bands increases two-fold for histidine gels, the resolution on a histidine gel has been actually improved by a factor of two over that obtainable on a standard Tris-borate gel.

For DNA lengths greater than 70 nucleotides, the sharpness of the bands on a histidine gel deteriorates It is difficult to identify bands on a sequencing type 9el that correspond to lengths greater than 100 nucleotides, and bands corresponding to DNA molecules longer than 150 nucleotides long tend to smear.

It may be that the main cause of these effects is the charge heterogeneity of the DNA-counterion complex for a DNA molecule of any given length in a given buffer. The charge of a DNA molecule in a buffer is less than the formal charge (number of phosphate groups) due to counterion condensation. The uncompensated charge may be as little as 24% of the formal charge in aqueous $Na^+$ or 12% in $Mg^{2+}$ environments. Manning, G. S. The Molecular Theory of Polyelectrolyte Solutions with Applications to the Electrostatic Properties of Polynucleotides. *Quart. Rev. Biophys.* 11:179–246 (1978). The uncompensated charge depends weakly on ionic strength, and determines the electrostatic force exerted on the DNA molecule and determines the migration rate of the molecule within the gel. The half-width of the DNA band on a gel will be determined by the degree of variability of uncompensated charge on DNA molecules of a given length in the buffer. Exactly how the buffer composition affects this variability is unknown.

EXAMPLE 6

Other Polycationic Buffers

Other polycationic compounds have been tested as buffer constituents for the improved resolution of DNA gels. A histidine molecule may assume one of two ionic forms at pH 7.6. Since the imidazole group has $pK_a = 6.0$, most histidine molecules in solution are zwitterions ($NH_3^+$ and $COO^-$) with no net charge. This accounts for the low conductivity of the histidine buffer. A fraction of the molecules, though, will have a protonated imidazole group. This class of molecules— polycations— is most likely the determinant of improved DNA separation. Indeed, the addition of 5 mM spermidine to 89 mM Tris-borate buffer increases the slope, α, from 0.7 to 1.3–1.5. For ethylenediamine, the slope, α, ranged from 1.6 to 1.8 at a pH of 11. However, for both of these buffers, the DNA bands formed are less distinct than the bands obtained using histidine, and these buffers may not be useful for all purposes. Buffers containing imidazole gave similar resolution results. Thus, while histidine is the most preferable buffer, other polycationic buffers, particularly polyamines, polyamino acids and aliphatic polyamines, with low conductivity to lower the electrophoresis time, may also provide improved separation of nucleic acids on gels.

EXAMPLE 7

Conductivity of a gel solution with 50 mM L-histidine, but without ammonium persulfate, is about 1/10 the conductivity of 89 mM Tris-borate buffer, pH 8.3. The implication is that if the two types of gels are run at the same temperature, or at the same power, electrophoresis on the histidine gel would take ⅓ the time required to accomplish electrophoresis on a Tris-borate gel, since a three-fold higher voltage may be applied. The reduction of electrophoresis time was confirmed experimentally. For longer (40 cm), thin (0.4 mm), sequencing type gels, acceptable voltages may reach or exceed 5000 volts. Therefore, typical running times may be reduced from 3 hours to 1 hour.

The foregoing illustrative examples relate to the improved resolution of gel electrophoresis of DNA obtainable using polycationic buffers. Preferred polycationic buffers include polyamines such as histidine, spermidine and ethylenediamine. In addition, Tris-borate or ethylenediamine tetra-acetate may be included in the buffer. Improved resolution for the gel electrophoresis of nucleic acids ranging in length from a few to about 70 nucleotides long may be obtained using a buffer consisting essentially of histidine. More preferably, the histidine buffer concentration is within the range of from 10 mM to 100 mM, the polyacrylamide gel has a percent cross-link concentration of from 8% to 20%, and the buffer has a conductivity ranging from 20 to 200 $mOhm^{-1}$. Most preferred is a histidine buffer concentration of 50 mM, a 12% cross-link polyacrylamide gel, and a conductivity of 100 $mOhm^{-1}$. It will be understood that a variety of techniques may alternatively be applied to provide various materials with properties which may be used in a similar manner. In addition, it will be understood that various modifications of the protocol presented may be adopted.

While the present invention has been described in terms of specific methods and compositions, it is understood that variations and modifications will occur to those skilled in the art upon consideration of the present invention. For example, it is envisioned that various polycationic compounds will be effective as buffers according to the present invention and that various concentrations of these compounds will be effective. Although the preferred polycationic buffers are histidine, ethylenediamine, and spermidine, it is not intended to preclude polycationic buffers such as polyamines, polyamino acids, aliphatic polyamines, polyhistidine, histidine derivatives and analogs or other polycationic buffers having low conductivity, not specifically mentioned or any other effective buffer or concentrations of these buffers from being included within the scope of the present invention.

Also, inasmuch as gels other than polyacrylamide gels have been successfully used in the gel electrophoresis separation of nucleic acids, and are, therefore, likely to be similarly effective, it is intended that these other gels such as agarose, methyl cellulose, and the like be included within the scope of the present invention as well.

Numerous modifications and variations of the invention described in the above illustrative examples are expected to occur to those skilled in the art and consequently only such limitations as appear in the appended claims should be placed thereon.

Accordingly, it is intended in the appended claims to cover all such equivalent variations which come within the scope of the invention as claimed.

What is claimed is:

1. A method for the gel electrophoresis of nucleic acids comprising the steps of:
    introducing a polycationic buffer to a gel; applying a sample of a nucleic acid on said gel; and
    applying an electromotive potential difference across said gel until resolution of said sample of a nucleic acid into its component parts.

2. The method as recited in claim 1 wherein the polycationic buffer is selected from the group consisting of polyamines, polyamino acids and aliphatic polyamines.

3. The method as recited in claim 1 wherein said step of introducing a polycationic buffer comprises the step of applying an aqueous solution of histidine at a concentration within a range of from 10 mM to 100 mM.

4. The method as recited in claim 1 wherein said step of applying a sample of denatured nucleic acid on a gel comprises the step of preparing a gel which is a polyacrylamide gel having a concentration of from 8% to 20% cross-linking.

* * * * *

UNITED STATES PATENT AND TRADEMARK OFFICE
CERTIFICATE OF CORRECTION

PATENT NO. : 4,936,963

DATED : June 26, 1990

INVENTOR(S) : W. Mandecki, et al.

It is certified that error appears in the above-identified patent and that said Letters Patent is hereby corrected as shown below:

In the drawings, Sheet 1 of 5:

Figure 1, insert --Fig. 1C-- above Fig. 1C--.

Column 5, Line 40, change "9el" to --gel--.

Signed and Sealed this

Third Day of September, 1991

*Attest:*

HARRY F. MANBECK, JR.

*Attesting Officer*   *Commissioner of Patents and Trademarks*